(12) United States Patent
Szelenyi et al.

(10) Patent No.: US 7,553,858 B2
(45) Date of Patent: Jun. 30, 2009

(54) COMBINATION OF FLUPIRTINE AND TRAMADOL

(75) Inventors: Istvan Szelenyi, Schwaig (DE); Joachim Maus, Muehlheim (DE); Peter J. Cnota, Homburg (DE)

(73) Assignee: MEDA Pharma GmbH & Co. KG, Bad Homburg (DE)

( * ) Notice: Subject to any disclaimer, the term of this patent is extended or adjusted under 35 U.S.C. 154(b) by 442 days.

(21) Appl. No.: 11/002,762

(22) Filed: Dec. 3, 2004

(65) Prior Publication Data

US 2005/0137235 A1 Jun. 23, 2005

Related U.S. Application Data

(60) Provisional application No. 60/529,761, filed on Dec. 17, 2003.

(51) Int. Cl.
*A61K 31/44* (2006.01)
*A61K 31/135* (2006.01)

(52) U.S. Cl. .................................. 514/352; 514/650

(58) Field of Classification Search ................ 514/352, 514/650
See application file for complete search history.

(56) References Cited

FOREIGN PATENT DOCUMENTS

CA 2314746 * 2/2001

OTHER PUBLICATIONS

Grond et al. High-dose tramadol in comparison to low-dose mrophine for cancer pain relief. Journal of Pain and Symptom Management. vol. 18, No. 3 Sep. 1999. pp. 174-179.*
Friedel et al. Flupirtine A review of its pharmacological properties, and therapeutic efficacy in pain states. Drug Evaluation, Drugs 45 (4): pp. 548-569, 1993.*

* cited by examiner

*Primary Examiner*—Jennifer Myong M Kim
(74) *Attorney, Agent, or Firm*—Crowell & Moring LLP

(57) ABSTRACT

The subject of the present invention is to provide a combination of two centrally acting analgesics, flupirtine and tramadol, or their respective pharmaceutically acceptable salts for the treament of pain.

21 Claims, No Drawings

COMBINATION OF FLUPIRTINE AND TRAMADOL

This application claims priority to U.S. Provisional Application Ser. No. 60/529,761, filed on Dec. 17, 2003, the entire contents of which are incorporated herein by reference.

The subject of the present invention is to provide a combination of two centrally acting analgesics, flupirtine and tramadol, or their respective pharmaceutically acceptable salts, for the treatment of pain.

Pain of multiple etiologies remains a substantial problem for many patients presented in the clinical setting.

The management of acute and chronic pain is important, not only for the patient's well-being, but also to prevent long-term complications and morbidity. Furthermore, acute pain may rapidly evolve into chronic pain if left untreated. Chronic pain remains a problem because it is often undertreated. Adverse effects and safety concerns associated with many analgesics have limited the use of these agents and contributed to the undertreatment of pain. With regard to drugs most commonly used to manage pain, centrally acting analgesics (e.g., morphine, codeine) are associated with respiratory depression, tolerance, and dependence, and most classical non-steroidal anti-inflammatory drugs (NSAIDs) produce adverse gastrointestinal effects.

Tramadol (trans-(+/−)-2-[(Dimethylamino)methyl]-1-(3-methoxyphenyl)cyclohexanol) is an analgesic agent with a dual mechanism of action, which includes weak agonistic effects at the opioid μ-receptor as well as inhibiting the neurotransmitter re-uptake (e.g. noradrenaline). Tramadol has a low affinity for opioid receptors and also inhibits noradrenaline (NA) and serotonin (5-HT) re-uptake within the pain pathways in the central nervous system. Tramadol's affinity for μ-receptors of the CNS remains low, being 6000 times lower than that of morphine and 10 times weaker than that of codeine (Raffa, J Clin Pharm Ther 2001; 26:257-64, Raffa et al., J Pharmacol Exp Ther 1992; 260:275-85, Lee et al., Drugs 1993; 46:313-40). The (+)-tramadol and its metabolite are selective agonists of μ-receptors (Raffa et al., J Pharmacol Exp Ther 1993; 267:331-40). The (−)-isomer mainly inhibits the NA re-uptake. Thus, the two enantiomers are complementary and synergistic (Raffa et al., J Pharmacol Exp Ther 1993; 267:331-40, Raffa, J Clin Pharm Ther 2001; 26:257-64). The same is valid for the pharmacodynamically active main metabolites (Garrido et al., J Pharmacol Exp Ther 2000; 295:352-9).

In the treatment of acute and chronic pain of various origins, tramadol has been demonstrated to be efficacious (i.e. Lewis and Han, Am J Health Syst Pharm. 1997 Mar 15;54(6):643-52, Hoogewijs et al., Eur J Emerg Med 2000; 7:119-23, Courtney and Cabraal, Arch Otolaryngol Head Neck Surg 2001; 127:385-8). Orally administered tramadol was found to be an effective analgesic in steps 2 and 3 of the World Health Organization's guidelines for the treatment of patients with cancer pain. However, tramadol is less effective for certain types of chronic pain, such as low-back pain (Lewis and Han, Am J Health Syst Pharm. 1997 Mar 15;54(6):643-52).

Apart from analgesia, tramadol administration may produce a constellation of symptoms (including dizziness, somnolence, nausea, constipation, vomiting, sweating, and pruritus) similar to that of an opioid (Silvasti et al., Eur J Anaesthesiol 1999; 16:834-9). Similarly to other opiates/opioids, tramadol causes respiratory depression (PDR, 2002). In rodent toxicity studies, clinical signs of intoxication were mainly behavioural disorders and convulsions (Matthiesen et al., Toxicol Lett 1998; 95:63-71). Accordingly, at higher doses and especially at children, tramadol can cause seizures.

The clinical popularity of opioids is limited to a certain extent by their propensity to cause muscular rigidity (muskuloskeletal hypertonia, PDR 2002). Opioid-induced muscle rigidity is also evident in laboratory animals as demonstrated by Havemann et al. (Life Sci 1982; 31:2319-22), Jerussi et al. (Pharmacol Biochem Behav 1987; 28:283-9), Nickel et al. (Arzn Forsch/Drug Res 1990a; 40:909-11, Arzn Forsch/Drug Res 1997; 47:1081-6). There is evidence from animal studies that tramadol, similarly to other opiates, can increase the tonus of skeletal muscle (Nickel et al., Arzn Forsch/Drug Res 1990a; 40:909-11, Arzn Forsch/Drug Res 1990b; 40:905-908, Arzn Forsch/Drug Res 1997; 47:1081-6). Tramadol's lacking muscle relaxing effect might explain its lower efficacy in the treatment of painful low back syndrome. The same may also be valid in patients with acute musculoskeletal pain (Turturro et al., 1998).

Tramadol has a potential to cause psychic and physical dependence of the morphine-type. The drug has been associated with craving, drug-seeking behavior, and tolerance development. Cases of abuse and dependence on tramadol have been reported (Senay et al., Drug Alcohol Depend 2003; 69:233-41). Tramadol should not be used in opioid-dependent patients. Tramadol can reinitiate physical dependence in patients that have been previously dependent or chronically using other opioids.

Flupirtine is a triaminopyridine derivative and is used as a non-opioid analgesic agent with muscle relaxant properties. It has been demonstrated that flupirtine reduced the skeletal muscle tone at doses comparable with its antinociceptive effective doses (Nickel et al., Arzn Forsch/Drug Res 1990a; 40:909-11). The mode of flupirtine's pharmacodynamic effects is related to its potassium channel opening activity, which might also explain flupirtine's functional NMDA-antagonistic activity. Additionally, flupirtine activates the descending noradrenergic pain-modulating pathways.

Since diazepam and other benzodiazepines are widely used as muscle relaxants it was obvious to compare the pharmacodynamic characteristics of flupirtine with those of benzodiazepines. In receptor binding studies, no affinity for specific [$^3$H]flunitrazepam binding was found up to 10 μmol/l (Nickel et al., Arzn Forsch/Drug Res 1990b; 40:905-908). There is evidence that flupirtine displays its antinociceptive activity via activation of noradrenergic descending pathways (Szelenyi et al., Ann Emerg Med 1998; 32:139-43). Recent investigations point out that flupirtine activates voltage independent potassium channels (Kornhuber et al., J Neural Transm 1999; 106:857-67). Besides the activation of descending noradrenergic pain-modulating pathways, this potassium channel opening effect of flupirtine may be responsible for its analgesic and skeletal muscle relaxing activity.

Flupirtine has been demonstrated to possess a significant antiepileptic potential (Kupferberg and Swinyard, Study Report, Report No. D-09998/FP2-01/00, Aug. 6, 1980, Viatris AG). This effect can be explained by its K$^+$-channel opening and functional NMDA-antagonistic properties.

Additionally, there is evidence that flupirtine is able to attenuate withdrawal symptoms of opiate-abuse (Nickel and Szelenyi, Luzern, Aug. 17-19, 1993, Regional Anesthesia 1993; 18(Suppl.):4).

Flupirtine can effectively be used in the management of painful disorders such as pain resulting from episiotomy, surgical or dental procedures (McMahon et al., Postgrad Med J 1987; 63(Suppl 3):81-5), posttraumatic pain, cancer, rheumatic diseases (e.g. arthrosis, arthritis), neuralgia, dysmenorrhoe, in elderly patient with osteoporosis (Ringe et al., Arzneimittelforschung 2003; 53:496-502), migraine, headache, or tension headache (Worz et al., Fortschr Med 1995; 113:

463-8). It can also be used for disorders with increased skeletal muscle tone such as cervico-brachalgia, low back syndrome, ischio-lumbalgia. Additionally, for myofascial pain, flupirtine is to be recommended because of its analgetic and muscle-tone-normalizing actions (Worz et al., Fortschr Med 2000; 142:27-33).

It is often difficult to achieve complete pain control using a single drug. There are numerous drugs on the market, their clinical usefulness, however, is often questionable or limited by their undesired effects. In certain cases, meaningful combinations may overcome possible undesired effects of mono compounds. In addition, there are several painful diseases which are often accompanied by increased skeletal muscle tone. As a consequence, it is often necessary to reduce the increased skeletal muscle tone, as well. The therapy of such disorders involves for example benzodiazepines which have, however, a pronounced abuse potential and therefore their administration is very limited.

Improved pain relief can be demonstrated, and adverse effects minimized, by multimodal analgesic combinations. Substantial evidence supports combining analgesics for the management of pain and, in some instances, they have a heterogeneous pharmacodynamic sparing effect. Fixed-dose combination analgesics with demonstrated efficacy and safety are widely useful for pain management (i.e. McClellan and Scott, Drugs 2003; 63:1079-86, Wilder-Smith et al. Anesth Analg 2003; 97:526-33). Sometimes, combinative administration of tramadol with NSAIDs such as diclofenac appears to be less advantageous, because oral application of diclofenac significantly delayed fracture healing in rats. This effect might be comparable to other NSAIDs and fracture healing in humans (Beck et al., Arch Orthop Trauma Surg 2003; 123:327-32).

The problem underlying the present invention was therefore the presentation of a drug combination for the treatment of pain providing improved efficiency and reduced side effects. A solution is given by the combination of tramadol and flupirtine or their respective pharmaceutically acceptable salts.

The present invention shows that, based on the pharmacodynamic properties of opiate μ-receptor influencing compounds (i.e. tramadol) and the potassium channel opener flupirtine, the antinociceptive/analgesic activity of tramadol or flupirtine can be intensified by combining both drugs.

In combination less amounts of the drugs are enough to produce the same analgesic effect as if either of the drugs was used alone. Surprisingly, the analgesic effect of the combination is of overadditive nature. By using less amounts of both drugs the side effects associated with each are reduced in number and degree. Additionally, flupirtine abolishes the increase in skeletal muscle tone, a typical opioid effect. Furthermore, flupirtine does not cause any respiratory depression, a typical side effect of tramadol and other opiates/opioids. Moreover, flupirtine is able to reduce symptoms following opiate withdrawal. Due to its anticonvulsive effect, flupirtine can attenuate the possible convulsive action of tramadol.

Additionally, the skeletal muscle relaxing activity of flupirtine abolishes the muscle tone increasing effect of tramadol. Furthermore, it is known that tramadol can cause seizure. On the other hand, it is also known that flupirtine possesses anticonvulsant activities. Thus, flupirtine can compensate the possible convulsive activity of tramadol resulting in a better acceptance of the combination. It is known that tramadol can induce respiratory depression. Because the dose of tramadol can be reduced in the combination with flupirtine, the risk of a possible respiratory depression caused by tramadol is considerably diminished.

EXPERIMENTAL DATA

Part 1: Antinociceptive Effects on Acetylcholine-Induced Writhing in Mice

Male mice weighing 22-24 g were maintained in groups of 4 at standard conditions (temperature 22±1° C., humidity: 40-50%, dark-light rhythm: 12/12 h) with food and water freely available. All protocols were approved by the Animal Health Committee which is responsible for the care and proper use of experimental animals.

Abdominal contractions (writhings) were induced by intraperitoneal (i.p.) injection of acetylcholine (ACh) (chloride, 5.5. mg/kg) in a volume of 10 ml/kg. Immediately thereafter, mice were placed in a plastic cage and the number of abdominal contractions (writhes) was counted for 10 min. The total number of abdominal contractions per animal and number of animals with contractions were calculated.

Drugs were prepared daily. All compounds were given orally. Tramadol hydrochloride and flupirtine maleate were administered 30 min before acetylcholine injection.

$ED_{50}$ values were estimated either by the ratio of animals protected from writhings to the number of animals in groups or by the mean number of writhes in each group of animals. The values were calculated by using linear regression. The statistical analysis of differences between calculated and measured effects was carried out by the Kruscall-Wallis test. Asterisks (*) indicate the significance level $p<0.05$.

Both flupirtine and tramadol protected the animals from writhing and considerably reduced the number of writhings in conscious mice. The corresponding ED50-values are summarized in Table 1.

TABLE 1

Effect of orally administered flupirtine and tramadol on acetylcholine-induced writhing in mice.

| | oral $ED_{50}$-values calculated on the basis of | |
|---|---|---|
| | animals protected from writhings | reduction of number of writhings |
| Flupirtine | 27.25 | 21.00 |
| Tramadol | 4.87 | 4.14 |

Tables 2 and 3 summarize the results obtained following combined oral administration of various doses of flupirtine and tramadol.

TABLE 2

The effect of the combination flupirtine with tramadol on the acetylcholine-induced writhing in mice

| Treatment | | Number of animals without writhing in % | |
|---|---|---|---|
| | | calculated | measured |
| Flupirtine 5 mg/kg | +Tramadol 1 mg/kg | 39 | 60* |
| Flupirtine 5 mg/kg | +Tramadol 2 mg/kg | 50 | 70* |
| Flupirtine 5 mg/kg | +Tramadol 4 mg/kg | 73 | 90* |

TABLE 3

The effect of the combination tramadol with flupirtine
on the acetylcholine-induced writhing in mice

| Treatment | | Number of animals without writhing in % | |
|---|---|---|---|
| | | calculated | measured |
| Tramadol 2 mg/kg | +Flupirtine 5 mg/kg | 50 | 60* |
| Tramadol 2 mg/kg | +Flupirtine 10 mg/kg | 56 | 70* |
| Tramadol 2 mg/kg | +Flupirtine 20 mg/kg | 68 | 80* |

Data presented in Tables 2 and 3 clearly indicate that the antinociceptive effect of flupirtine has been reinforced in an overadditive manner by tramadol and vice versa, flupirtine reinforced the analgesic activity of tramadol in an overadditive way in conscious mice, as well.

Part 2: Influence of Tramadol and Flupirtine on Submaximal Pentetrazol-Induced Seizures in Mice It is known that tramadol can cause seizures at higher doses and especially in children. In rodent toxicity studies, it has also been demonstrated that tramadol may induce convulsions (Matthiesen et al.; Toxicol. Lett. 1998; 95; 63-7). Therefore, it was of interest to demonstrate that tramadol can influence seizures induced by subconvulsive doses of pentyletetrazol (pentetrazol). Furthermore, we have also investigated the effect of flupirtine on the pentetrazol-induced seizures.

Male mice weighing 22-24 g were used. Animals housed in groups of 4 at standard conditions (temperature 22° C., humidity 40-60%) with food and water freely available. Lights were on from 06.00 a.m. to 06.00 p.m. The experiments were approved by the Animal Health Committee of the University which is responsible for the care and proper use of experimental animals.

Seizures were induced by intraperitoneal administration of pentetrazol at the subconvulsive dose of 30 mg/kg. The latency of the first seizure reaction, the seizure intensity and the number of animals with seizures were calculated for the first 10 min after i.p. injection of pentetrazol. Tramadol (hydrochloride) and flupirtine (maleate) were given intraperitoneally (15 min before pentetrazol administration). Drugs were prepared daily in 0.9% saline.

TABLE 4

The effect of tramadol and flupirtine on seizures induced by
subconvulsive pentetrazol doses (30 mg/kg i.p.) in mice (n = 10).

| Treatment | | Intensity (scored) | Number of animals with seizures |
|---|---|---|---|
| Saline | — | — | 0.14 | 3 |
| — | Tramadol 20 mg/kg | — | 1.70* | 8* |
| — | Tramadol 40 mg/kg | — | 3.00* | 10* |
| — | — | Flupirtine 10 mg/kg | 0.20 | 2 |
| — | — | Flupirtine 20 mg/kg | 0.10 | 1 |
| — | Tramadol 20 mg/kg | Flupirtine 10 mg/kg | 0.30# | 2# |
| — | Tramadol 20 mg/kg | Flupirtine 20 mg/kg | 0.30# | 1# |
| — | Tramadol 40 mg/kg | Flupirtine 10 mg/kg | 0.40# | 3# |
| — | Tramadol 40 mg/kg | Flupirtine 20 mg/kg | 0.30# | 2# |

*significant (p < 0.05) (compared with the saline-treated group)
significant (p < 0.05) (compared with the tramadol-treated animals)

Results summarized in Table 4 indicate that in contrast to flupirtine, tramadol possesses proconvulsive effects on the model of acute seizures induced by subconvulsive doses of pentetrazol; and flupirtine counteracts this effect of tramadol. In the combination, flupirtine almost completely attenuated the proconvulsive activity of tramadol.

Part 3: Changes in the Skeletal Muscle Tone in Conscious Rats Following Intraperitoneal Administration of Tramadol and Flupirtine, Alone and in Combination The experimental set-up has been described in all details in a former publication (Nickel et al. Arzn. Forsch./Drug Res. 1997; 47; 1081-6). Briefly, the measurement of skeletal muscle tone was done by recording successively the resistance of flexor and extensor muscles which counteracted the forced straightening and bending of the foot in the ankle joint. Pressure changes induced by the movements of the foot were continuously registered. Signals were analyzed on a personal computer. A corresponding computer program calculated the resistance values of flexors and extensors of the foot over 10 min recording periods.

Male Sprague-Dawley rats weighing 200-220 g were used. Animals housed in groups of 2 at standard conditions (temperature 22° C., humidity 40-60%) with food and water freely available. Lights were on from 06.00 a.m. to 06.00 p.m. All protocols were approved by the Animal Health Committee which is responsible for the care and proper use of experimental animals.

Drugs (tramadol hydrochloride, flupirtine maleate) were prepared in physiological saline daily and given intraperitoneally.

The statistical analysis of differences between calculated and measured effects was carried out by the one-way ANOVA. Asterisks (*) indicate the significance level p<0.01.

The dose-dependent enhancement of the skeletal muscle tone by intraperitoneally given tramadol has been demonstrated in earlier studies (Nickel et al. Arzn Forsch/Drug Res 1990; 40; 909-11). Flupirtine (5-10 mg/kg i.p.) completely abolished tramadol-induced skeletal muscle rigidity in conscious rats (Table 5).

TABLE 5

Effect of intraperitoneal administered tramadol and flupirtine
on the skeletal muscle tone in conscious rats.

| Treatment | | Changes in muscle tonus (in % compared to placebo) |
|---|---|---|
| Tramadol 20 mg/kg | — | +12% |
| Tramadol 40 mg/kg | — | +47%* |
| Tramadol 20 mg/kg | Flupirtine 10 mg/kg | −14%* |
| Tramadol 40 mg/kg | Flupirtine 10 mg/kg | −12%* |

Data presented in Table 5 clearly indicate that tramadol increases the skeletal muscle tone. Flupirtine was able to attenuate the skeletal muscle rigidity induced by tramadol.

Part 4: Emetic Effects of Tramadol and Flupirtine in Dogs

Mongrel dogs of both sexes weighing up to 15 kg were used. They were deprived of food overnight but allowed water ad libitum. Test compounds were administered to conscious animals by a slow infusion via the saphenous vein. Emetic responses (retches, strong salivation vomits with output) were monitored 60 min following drug administration (Borison and Wang, 1953). All dogs received 14 mg/kg tramadol i.v. repeatedly with an interval of one week. Positive responder dogs were selected and used in further experiments.

As shown in Table 6, tramadol induced emetic response in all dogs. Flupirtine, at the dose of 7 mg/kg i.v. caused emesis in 3 of 5 dogs. When tramadol was administered in combination with flupirtine (given immediately after administration of tramadol), the emetic response induced by tramadol was considerably reduced or completely abolished.

TABLE 6

The effect of flupirtine on the tramadol-induced emesis in conscious mongrel dogs (n = 5).

| Treatment | Emetic response* | |
|---|---|---|
| Saline | in none of 5 dogs | 0% |
| Tramadol 14 mg/kg, i.v. | in 5 of 5 dogs** | 100% |
| Flupirtine 7 mg/kg, i.v. | in 3 of 5 dogs | 60% |
| Flupirtine 7 mg/kg, i.v. + Tramadol 14 mg/kg, i.v. | in 1 of 5 dogs | 20% |
| Flupirtine 1 mg/kg, i.v. + Tramadol 14 mg/kg, i.v. | in none of 5 dogs | 0% |

*emetic response was monitored during the first 60 min after drug administration
**these responder dogs were used thoroughly in all experiments Data presented in Table 6 clearly indicate the surprising "antiemetic" effect of flupirtine when it was given in combination with tramadol administered at the high emetogenic dose of 14 mg/kg.

The combination of tramadol and flupirtin or their respective salts shows increased efficiency with an overadditive effect in the treatment of pain in lower doses than each compound alone. Side effects as convulsion, increased muscle tone and emesis are reduced simultaneously.

Therefore, the combination according to the invention can be useful in the treatment of painful disorders of various origin such as cancer, rheumatic diseases (e.g. arthrosis, arthritis), (tension) headache, migraine, painful musculoskeletal disorders with hypermyotonia and decreased motility, e.g. disk prolapse, disk protrusion or other intervertebral disk lesions as intervertebral chondrosis and osteochondrosis, cervical myelopathy, vertebral dysplasia, cervico-brachalgia, low back syndrome, and ischio-lumbalgia; and those resulting from spinal cord injuries, osteoporosis, rigidity/spasticity, neuropathy/neuralgia (e.g. myofascial pain, trigeminal neuralgia, shingles neuralgia), dental pain, post-traumatic pain (e.g. bone fracture), in the post-surgical treatment and in the treatment of lower spastic paraperesis syndrome or tetrapareses (e.g. lower paraspasmus, transversal myelitis, multiple sclerosis, hereditary spastic paraplegia inferior (Stuempel paraplegia), disturbances of the spinal blood circulation, cerebral palsy with lower spastic paresis) or in the treatment of biliary or renal colic.

The compounds of the combination according to the invention can be administered simultaneously or sequentially or in a fixed combination. They may be given together in a single dosage form. Or they may be administered as two formulations which may be the same or different. They may be given at the same time (simultaneously) or they can be administered either close in time or remotely, such as where flupirtine is given in the evening and tramadol is given in the morning.

The combination according to the invention may be administered orally, rectally, intravenously, transdermally, subcutaneously or intracutaneously.

The combination of tramadol and flupirtine or their respective pharmaceutically acceptable salts can be formulated for example as tablets, syrups, drops, capsules, controlled-release preparation, lozenges, pellets, powder, granulate or effervescent formulations. When a tablet is used, any pharmaceutical carrier routinely used for solid formulations may be used. Examples for such carriers include magnesium stearate, terra alba, talc, gelatin, acacia, stearic acid, starch, lactose and sucrose. A syrup formulation will generally consist of a suspension or solution of the compound or its salt in a liquid carrier for example, ethanol, peanut oil, olive oil, glycerin or water with a flavoring or coloring agent. When the composition is in the form of a capsule, any routine encapsulation is suitable, for example using the aforementioned carriers in a hard gelatine capsule shell. Where the composition is in the form of a soft gelatine shell capsule, any pharmaceutical carrier routinely used for preparing dispersions or suspensions may be considered, for example aqueous gums, celluloses, silicates or oils, and incorporated in a soft gelatine capsule shell. In order to lengthen the duration of the pharmacodynamic effect, one or both components of the combination preparation can also be retarded. Furthermore, the combination can be administered rectally by using suppositoria.

The active ingredients of the combination according to the invention may be given from 1 to 8 times a day, sufficient to exhibit the desired activity. Preferably, the active components are given about once or four times a day, more preferably twice a day.

As for the amount of drug administered, tramadol can be administered in conformity with approved labeling in an amount of between 50 and $\geq$400 mg/day adult human with the preference of 100 to 400 mg/day in dependence of the pain intensity. Flupirtine can be administered in conformity with approved labeling in an amount of 100 to 800 mg/day with the preference between 200 and 400 mg/day.

As for the amount of drug administered in a retarded form, tramadol can be administered in conformity with approved labeling in an amount of between 100 and 400 mg/day adult human with the preference of 50 to 200 mg/day in dependence of the pain intensity. Flupirtine can be administered in conformity with approved labeling in an amount of 100 to 600 mg/day with the preference between 100 and 200 mg/day.

The following pharmaceutical dosage forms give examples of the presentation of the combination according to the invention without limiting it.

The combination contains 1 part of flupirtine and 1 part of tramadol. The single dose for tramadol amounts to 10-50 mg/dose. The single oral dose for flupirtine amounts to 50-100 mg/dose. The combination can be given once to eight times per day.

The sustained release combination contains 1 part of retarded flupirtine and 1 part of retarded tramadol. The single dose for tramadol amounts to 50-200 mg/dose. The single oral dose for flupirtine amounts to 100-200 mg/dose. The combination can be given once to two times per day.

The invention claimed is:

1. A method for the treatment of pain comprising administering effective amounts of flupirtine in combination with tramadol or their respective physiologically acceptable salts to a patient in need of such treatment, wherein the combination of flupirtine and tramadol intensifies their antinociceptive/analgesic activities.

2. The method according to claim 1 where the pain is caused by increased skeletal muscle tone.

3. The method according to claim 1 where the pain is caused by pain in cancer.

4. The method according to claim 1 for the treatment of rheumatic pain.

5. The method according to claim 1 where the pain is caused by painful musculosketal disorders with hypermyotonia and decreased motility.

6. The method according to claim 1 where the pain is caused by neuralgia and/or neuropathy.

7. The method according to claim 1 for the treatment of chronic or episodic or tension headache or migraine.

8. The method according to claim 1 for the treatment of post-surgical or post-traumatic pain and dental pain.

9. The method according to claim 1 where the pain is caused by lower spastic paraperesis syndrome or tetrapareses.

10. The method according to claim 1 where the pain is caused by biliary or renal colic.

11. A method for the treatment of pain comprising administering effective amounts of flupirtine in combination with tramadol or their respective physiologically acceptable salts in an oral, rectal, intravenous, transdermal or subcutaneous or intracutaneous form to a patient in need of such treatment, wherein the combination of flunirtine and tramadol intensifies their antinociceptive/analgesic activities.

12. The method according to claim 1, wherein the daily dosage for tramadol is 50 to 400 mg/day and that the daily dosage of flupirtine is 100 to 800 mg/day.

13. The method according to claim 1, wherein the daily dosage for tramadol is 100 to 400 mg/day and the daily dose of flupirtine is 200 to 400/mg day.

14. The method according to claim 4, wherein the rheumatic pain is caused by arthrose and/or arthritis.

15. The method according to claim 5, wherein the pain is caused by disk relapse, disk protrusion, inervertebral disk lesions, intervertebral chondrosis, osteochondrosis, cervical myelopathy, vertebral dysplasia, cervico-brachalgia, low bak syndrome, and/or ischio-lumbalgia.

16. The method according to claim 5, wherein the pain results from spinal cord injuries, osteoporosis, rigidity and/or spasticity.

17. the method according to claim 6, wherein the pain is myofascial pain.

18. The method according to claim 6, wherein the pain is caused by trigeminal neuralgia and/or shingles neuralgia.

19. The method according to claim 8, wherein the post-traumatic pain is caused by bone fracture.

20. The method according to claim 9, wherein the pain is caused by lower paraspasmus, transversal myelitis, multiple sclerosis, hereditary spastic paraplegia inferior, Stuempel paraplegia, disturbances of the spinal blood circulation, and/or cerebral palsy with lower spastic paresis.

21. The method according to claim 1, wherein the effective amount of flupirtine is sufficient to reduce emesis induced by the tramadol.

* * * * *